US005747674A

United States Patent [19]

Moracchini et al.

[11] Patent Number: 5,747,674
[45] Date of Patent: May 5, 1998

[54] DEVICE FOR PERFORMING THERMODYNAMIC MEASUREMENTS ON MULTIPHASE FLUIDS AT VERY HIGH PRESSURES AND TEMPERATURES

[75] Inventors: Gérard Moracchini, Andilly; José Sanchez, Viarmes; Jean-Charles de Hemptinne, Vésinet; Philippe Ungerer, Le Vésinet, all of France

[73] Assignee: Institut Francais du Petrole, Rueil-Malmaison, France

[21] Appl. No.: 640,740

[22] PCT Filed: Sep. 4, 1995

[86] PCT No.: PCT/FR95/01146

§ 371 Date: May 6, 1996

§ 102(e) Date: May 6, 1996

[87] PCT Pub. No.: WO96/07902

PCT Pub. Date: Mar. 14, 1996

[30] Foreign Application Priority Data

Sep. 9, 1994 [FR] France ................... 94 10784

[51] Int. Cl.$^6$ ........................................ G01N 33/20
[52] U.S. Cl. .......................... 73/61.44; 73/152.18
[58] Field of Search ............... 73/864.62, 152.18, 73/152.42, 61.44, 53.05

[56] References Cited

U.S. PATENT DOCUMENTS

| | | | |
|---|---|---|---|
| 4,425,810 | 1/1984 | Simon et al. | 73/863.11 |
| 4,530,234 | 7/1985 | Cullick et al. | 73/53 |
| 4,852,395 | 8/1989 | Kolpak | 73/61.1 R |
| 4,924,695 | 5/1990 | Kolpak | 73/61.1 R |
| 5,536,474 | 7/1996 | Ungerer et al. | 422/100 |
| 5,540,087 | 7/1996 | Bickert et al. | 73/53.05 |

Primary Examiner—Hezron E. Williams
Assistant Examiner—Jay L. Politzer
Attorney, Agent, or Firm—Antonelli, Terry, Stout, & Kraus, LLP

[57] ABSTRACT

The fluids to be studied are placed in a chamber (13) of variable volume delimited by a piston (5) that can be moved by hydraulic device (24) in a cavity of a body (1). An endoscope (18) allowing to view the inside of the chamber and notably to see the orifices of two diametrically opposite pipes (14, 15) that communicate the cell with the outside is placed behind a transparent porthole (8) closing the end of the chamber opposite the piston. The body (1) can swivel about a pin (26), which allows achievement of equilibrium and also to draw off a particular phase of a stratified multiphase fluid by placing the orifice of one of pipes (14, 15) within this phase. A pressure detector (19) is included in the wall of the piston so as to decrease practically any dead volume likely to distort the measurements. A single body can contain two cells placed side by side, at least one having a transparent wall. The device can be used for studying fluids, notably petroleum fluids.

21 Claims, 2 Drawing Sheets 5,747,674

DEVICE FOR PERFORMING THERMODYNAMIC MEASUREMENTS ON MULTIPHASE FLUIDS AT VERY HIGH PRESSURES AND TEMPERATURES

BACKGROUND OF THE INVENTION

1. Field of the Invention

The present invention relates to a device for measuring thermodynamic properties of fluid samples at a very high pressure and at a high temperature, notably corrosive fluids.

2. Description of the Prior Art

The assignee's French patent FR-2,666,415 describes a device intended to carry out measurement operations on samples. It mainly comprises a climatic enclosure in which is placed a body including two cylindrical chambers of variable volume limited respectively by two mobile pistons. One of the chambers is provided with a transparent wall in order to facilitate the complete transfer of a phase of the sample towards the other chamber. A driving device is associated with the two pistons in order to move them in an independent or coordinated way. The device is operated by a micro-computer.

The assignee's French patent application FR-93/10,896 also describes a device for transferring samples under pressure, comprising a draw-off cell facilitating transfer operations of samples towards measuring devices exterior to a climatic enclosure.

SUMMARY OF THE INVENTION

The device according to the invention is suitable for many applications. It can notably be used with the scope of thermodynamic property studies for samples originally taken from wells drilled in underground reservoirs and subjected on the surface to pressure and temperature conditions that reproduce the conditions prevailing in the places where they were taken. These samples notably contain hydrocarbons, brines, carbon dioxide, hydrogen sulfide, etc. It can also be used for chemical engineering applications for the study of polymer solutions for example.

The object of the measurements is notably to assess the petroleum effluent content of the samples. The thermodynamic properties are calculated by using composition models in which data obtained through analysis of the samples are integrated. Certain parameters such as the pressure and the temperature for example are varied from values reproducing those existing at the production depth to those prevailing at the surface. Analysis methods of this type make it possible to measure important properties such as saturation pressures.

The samples are generally isolated in devices including a thermostatically controlled enclosure or drying oven, having one or several containment cells, suited to maintain each cell under pressure conditions analogous to those prevailing at the production depth. Certain measuring operations make it necessary to obtain a fraction of the samples contained in the containment cells while inside the enclosure. For easy handling and measurement precision, it is important to abide by certain conditions:

the samples must preferably be taken under the pressure and temperature conditions that prevail in the thermostatically controlled enclosure, the draw-off cell must therefore be simply coupled with the cell containing the substance to be taken so that it can be freed in the same way thereafter;

the volume drawn off must be known with precision so as to be able to measure easily its density and so that it can practically entirely be transferred into other measuring devices; and the operations designed to draw off the fraction and then to transfer it to a measuring device such as a gasometer must be carried out automatically so that set values can be easily maintained.

The device according to the invention provides an operator the opportunity to perform very precise measurement operations on fluid samples extracted from underground, possibly corrosive fluids, kept at high pressures that can reach 130 to 150 MPa (mega pascals) and at high temperatures that can reach 250° C. or even more.

The device comprises a thermostatically controlled climatic enclosure, a rigid containment body placed in the enclosure, provided with at least one elongated containment chamber of variable volume for fluid samples, limited by a mobile piston in a direction of elongation and a device of controlled communication with the outside of the chamber.

It comprises a transparent block made of sapphire for example, limiting the containment chamber on a side opposite the mobile piston, a seal for fastening the transparent block to the body, a display for viewing the inside of the chamber through the transparent block, pipes controlled by valves, opening into the chamber in proximity of the transparent block and laterally shifted on either side of the direction of elongation of the containment chamber.

The display comprises for example an endoscope associated with the transparent block, allowing the operator to see the orifices of the pipes opening into the containment chamber.

According to a preferred embodiment, the device comprises an element for measuring the pressure prevailing in the chamber, that is placed in a recess provided in the mobile piston. The measuring element used is advantageously a flush-membrane pressure detector mounted on the mobile piston so as to improve the sensitivity thereof.

With this layout, the pressure in the chamber remains measurable until the mobile piston has completely traveled into the chamber. Dead volumes, that are inevitable when the pressure measuring device is placed outside the chamber, as it is generally the case, and connected thereto by a particular pipe, are also avoided.

According to an advantageous embodiment, the device comprises a mechanism for swivelling the cell about a pin perpendicular to the direction of elongation of the cell.

This layout is notably useful when fluid samples comprising stratified phases are studied. When the pipes opening into the containment chamber are laterally shifted, a sufficient inclination of the cell through swivelling of the pin has the effect of causing the pipes to open into two different phases and therefore to allow selective draw-offs. A lateral inclination of the cell, on one side or the other, improves the observer's vision of the orifice of the two pipes.

The alternate swivelling of the pin allows a perfect homogenization of the samples.

The device can include an optical device for measuring the displacements of the mobile piston, which offers a great precision in the measurement of the volumes.

According to another embodiment, the device comprises, in the same rigid body, a second containment chamber limited by a second mobile piston, this second chamber being provided with at least one pipe controlled by a valve, and a distribution device for communicating with the pipes associated with the two chambers with one another and with the outside of the body.

The second chamber can be identical to the first chamber with two pipes laterally spaced apart from one another and a measuring device in the mobile piston, and also possibly a transparent block for limiting the bottom thereof.

According to an embodiment, the two containment chambers can be adjacent.

BRIEF DESCRIPTION OF THE DRAWINGS

The layout of the device according to the invention will be clear from reading the description hereafter of embodiments given by way of non limitative examples, with reference to the accompanying drawings in which.

DESCRIPTION OF THE PREFERRED EMBODIMENTS

Figure 1:
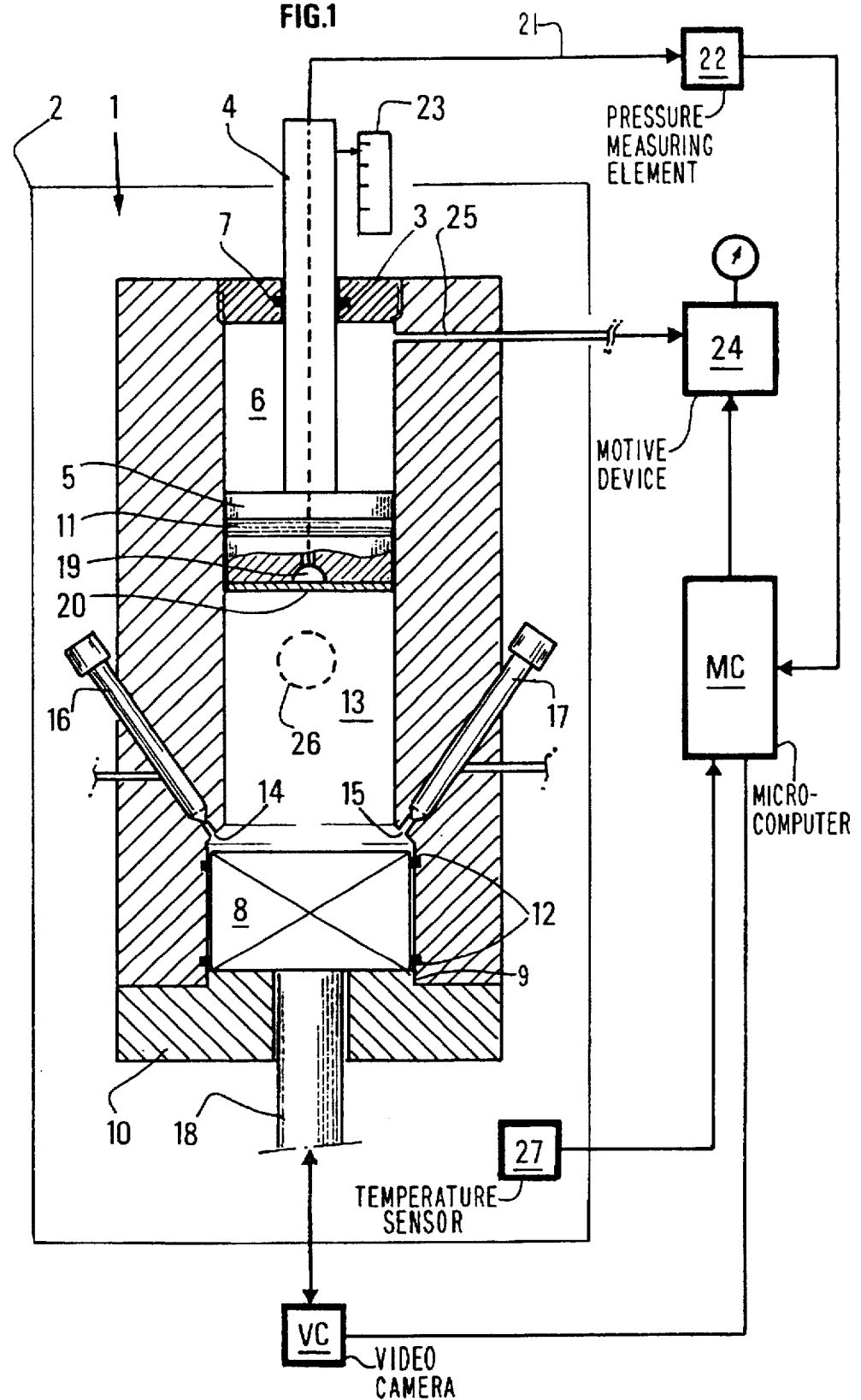
FIG. 1 diagrammatically shows a containment body with a single chamber in accordance with the invention FIG. 2 diagrammatically shows a containment body with two adjacent chambers in accordance with invention and FIG. 2A diagrammatically shows a sample draw-off cell such as that described in the above-cited French patent application.

The containment cell illustrated schematically in FIG. 1 comprises a hollow elongated cylindrical body 1 that is placed during operation in a thermostatically controlled enclosure 2 of a well-known type. At a first end, cylindrical body 1 is closed by a threaded cap 3 through which an opening extends whose section is suited to that of the rod 4 of a piston 5 that can be shifted in the inner cavity 6. A seal 7 of a well-known type for withstanding high pressures is arranged around rod 4 so as to isolate the inner cavity 6 of inner chamber 13. At the opposite end thereof, cylindrical body 1 is closed by a thick disk or block 8 made from a transparent material such as sapphire for example, that is pressed against an inner shoulder 9 of the inner cavity 6 by a fastening end 10. Seals 11 and 12 also suited to very high pressures are placed respectively around piston 5 and transparent disk 8 so as to isolate the variable-volume inner chamber 13 limited by cylindrical body 1 between disk 8 and mobile piston 5.

Two slender pipes 14 and 15 respectively associated with two control needle valves 16, 17 terminate in the vicinity of the cell base, on the side of transparent disk 8. The orifices of these two pipes 14 and 15 are laterally shifted with respect to one another and preferably are diametrically opposite.

Fastening end 10 comprises an opening for the passage of a display device 18 such as an endoscope of a well-known type, whose end rests against porthole 8. A video camera VC is associated with endoscope 18. The latter is mounted swivel with respect to body 1. By inclining it on either side of the axis of the cylinder, the inner volume and notably draw-off pipes 14 and 15 can be better viewed.

The flush pressure prevailing in chamber 13 is measured by a pressure detector 19 mounted on piston 5. Membrane 20 separates the pressure detector from variable-volume chamber 13. It is housed for example in a cavity provided in piston 5 along the axis thereof. Electrical conductors passing through a fine channel along the axis of rod 4 connect detector 19 to its associated measuring element 21.

The displacements of piston 5, directly proportionate to the volume of chamber 13, are measured by an optical element 23 of the optical rule type for example.

A hydraulic device such as a double-acting pump 24, communicating with the inside of cavity 6 by means of a channel 25 that ends up behind piston 5, are used for moving the latter and for varying the volume of chamber 13.

The cell is secured to a pin 26 perpendicular to its axis of elongation. A motive device (not shown) allows pin 26 to swivel the cell alternately in one direction and in the opposite direction. The angular amplitude of the swivelling can reach 300° for example.

The alternating swivelling of the cell can be used to bring the multiphase sample into equilibrium in the cell.

A swivelling of controlled amplitude also facilitates observations:

a) When the sample in chamber 13 consists of a multiphase fluid with stratified phases, a sufficient inclination of the cell can have the effect of shifting the orifices of pipes 14, 15 respectively within two of the phases. A selective extraction of one or the other can thus be performed through a controlled opening of valves 16 or 17.

b) The inclination of the cell also has a useful effect insofar as it moves the interface level opposite endoscope 18, which improves the observer's control possibilities.

The device also comprises a temperature pickup 27. All the measuring device 19, 21 and 27, the video camera VC and the hydraulic motive device 24 are controlled by a micro-computer MC.

Figure 2:
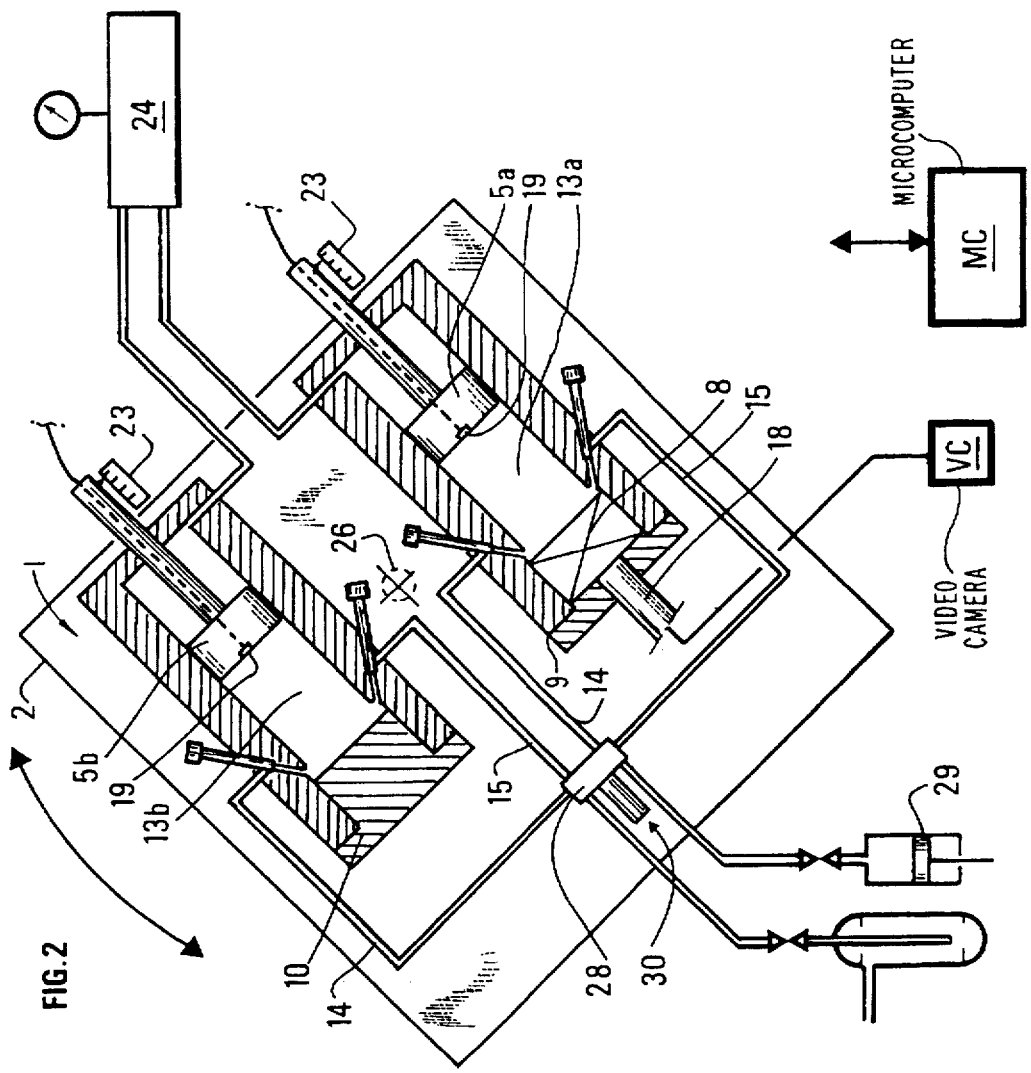
Figure 2A:
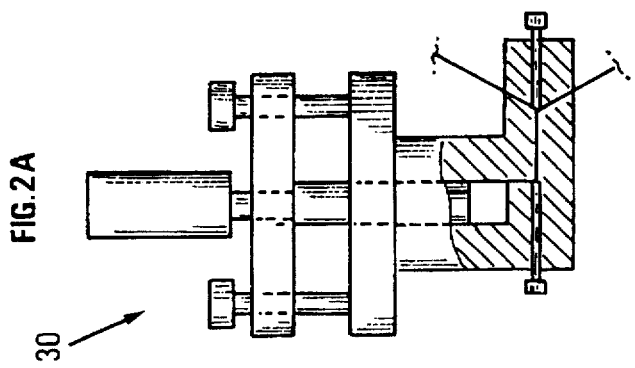

According to the embodiment of FIG. 2, the device comprises a rigid body 1 with two containment cells of parallel axes placed side by side for example. The two cells include a chamber (13A and 13B) of variable volume limited by a piston (respectively 5a and 5b) sliding in a cavity of the body and driven by hydraulic device 24. An optical rule 23 for measuring the displacement and a pressure detector 19 are associated with each piston.

Chamber 13a is analogous to that shown in FIG. 1 with its thick porthole 8 associated with a visual observation device 18.

The second cell has no visual control means such as 8 and 18 with the bottom of chamber 13b consisting of a solid end 10.

The pipes 14 and 15 coming from chambers 13A and 13B end at a manifold 28. Operating it allows the control of selective transfers of phases between the two chambers and/or to communicate them with outside devices such as a solvent injection pump 29. A draw-off cell 30, such as that described in the above-cited French patent, can also be connected to this manifold 28.

Body 1 is similarly moved about a swivelling pin 26 to allow homogenization of the samples or to facilitate their control. The various measuring device in both chambers 13A and 13B, the motive device driving pistons 5A and 5B, pin 26, and manifold 28 are controlled by micro-computer MC.

We claim:

1. A device for measuring thermodynamic properties of a fluid sample at high pressures and high temperatures including a corrosive fluid sample comprising: a thermostatically controlled enclosure, a rigid containment body placed in the enclosure, provided with at least one elongated containment chamber of variable volume for containing the fluid sample, limited by a piston moving along a direction of elongation of the at least one elongated containment chamber and a control for controlling communications with outside of the at least one elongated containment chamber, a transparent block forming a terminal wall of one of the at least one elongated containment chamber, opposite the piston, a sealing device for fastening the transparent block to the rigid containment body, a display for viewing an inside of one of the at least one elongated chamber through the transparent block, a fluid control device including pipes controlled by valves, opening into the at least one elongated containment chamber in proximity of the transparent block and laterally shifted on either side of the direction of elongation of the at least one elongated containment chamber, and a device for selectively swivelling the at least one elongated containment chamber about a pin perpendicular to the direction of elongation of the at least one elongated containment chamber to shift an orifice of at least one of the pipes into or within a phase of the fluid sample.

2. A device as claimed in accordance with claim 1, comprising: an element for measuring a pressure prevailing in the one of the at least one elongated containment chamber, placed in a recess of the piston.

3. A device as claimed in claim 1, comprising: a pressure detector mounted flush on the piston for measuring pressure prevailing in the at least one elongated containment chamber which is separated from the variable volume by a membrane.

4. A device as claimed in claim 1, comprising: an optical device for measuring displacements of the piston.

5. A device as claimed in claim 1, wherein: transparent block is sapphire.

6. A device as claimed in claim 1, comprising: a second elongated containment chamber contained in the rigid containment body limited by a second piston, the second elongated containment chamber being provided with at least one pipe controlled by a valve, and a manifold for communicating with the pipes associated respectively with the first and second elongated containment chambers and with outside of the rigid containment body.

7. A device as claimed in claim 6, wherein: the first and second elongated containment chambers are placed beside each other.

8. A device for measuring thermodynamic properties of a fluid sample at high pressures and high temperatures including a corrosive fluid sample comprising: a thermostatically controlled enclosure, a rigid containment body placed in the enclosure, provided with at least one elongated containment chamber of variable volume for containing the fluid sample, limited by a piston moving along a direction of elongation of the at least one containment chamber and a control for controlling communications with outside of the at least one chamber, a transparent block forming a terminal wall of one of the at least one elongated containment chamber, opposite the piston, a sealing device for fastening the transparent block to the rigid body, a display for viewing an inside of the one of the at least one elongated containment chamber through the transparent block, a fluid control device including pipes controlled by valves, opening into the at least one elongated containment chamber in proximity of the transparent block and laterally shifted on either side of the direction of elongation of the at least one elongated containment chamber, and a device for alternately swivelling the at least one elongated containment chamber about a pin perpendicular to the direction of elongation of the at least one elongated containment chamber to accelerate bringing into equilibrium a multiphase sample.

9. A device as claimed in accordance with claim 8, comprising: an element for measuring a pressure prevailing in the one of the at least one elongated containment chamber, placed in a recess of the piston.

10. A device as claimed in claim 8, comprising: a pressure detector mounted flush on the piston for measuring pressure prevailing in the at least one elongated containment chamber which is separated from the variable volume by a membrane.

11. A device as claimed in claim 8, comprising: an optical device for measuring displacements of the piston.

12. A device as claimed in claim 8, wherein: transparent block is sapphire.

13. A device as claimed in claim 8, comprising: a second elongated containment chamber contained in the rigid containment body limited by a second piston, the second elongated containment chamber being provided with at least one pipe controlled by a valve, and a manifold for communicating with the pipes associated respectively with the first and second elongated containment chambers and with outside of the rigid containment body.

14. A device as claimed in claim 13, wherein: the first and second elongated containment chambers are placed beside each other.

15. A device for measuring thermodynamic properties of a fluid sample at high pressures and high temperatures including a corrosive fluid sample comprising: a thermostatically controlled enclosure, a rigid containment body placed in the enclosure, provided with at least one elongated containment chamber of variable volume for containing the fluid sample, limited by a side wall, a piston moving along a direction of elongation of the one of the at least one elongated containment chamber, forming a first end wall of the one of the at least one elongated containment chamber and a flat transparent block forming a second end wall of the one of the at least one elongated containment chamber, opposite the piston, a sealing device for fastening the transparent block to the body, a control for controlling communications with outside of the at least one elongated chamber, a fluid communication device including pipes, controlled by valves and having orifices opening through the side wall of the at least one elongated containment chamber in proximity of the transparent block on either side of a direction of the elongation of the one of the at least one elongated containment chamber and a display for viewing inside of the one of the at least one elongated containment chamber through the transparent block, and the display including an endoscope mounted to swivel to allow an operator to view the orifices of the pipes opening into the at least one elongated containment chamber.

16. A device as claimed in accordance with claim 15, comprising: an element for measuring a pressure prevailing in the one of the at least one elongated containment chamber, placed in a recess of the piston.

17. A device as claimed in claim 15, comprising: a pressure detector mounted flush on the piston for measuring pressure prevailing in the at least one elongated containment chamber which is separated from the variable volume by a membrane.

18. A device as claimed in claim 15, comprising: an optical device for measuring displacements of the piston.

19. A device as claimed in claim 15, wherein: transparent block is sapphire.

20. A device as claimed in claim 15, comprising: a second elongated containment chamber contained in the rigid containment body limited by a second piston, the second elongated containment chamber being provided with at least one pipe controlled by a valve, and a manifold for communicating with the pipes associated respectively with the first and second elongated containment chambers and with outside of the rigid containment body.

21. A device as claimed in claim 20, wherein: the first and second elongated containment chambers are placed beside each other.

* * * * *